United States Patent [19]

Mitsukuchi et al.

[11] Patent Number: 4,861,765
[45] Date of Patent: Aug. 29, 1989

[54] 21-ALKYL-, CYCLOALKYL- OR ARYL-SUBSTITUTED THIS STEROIDS AND PHARMACEUTICAL COMPOSITIONS CONTAINING THEM

[75] Inventors: Morihiro Mitsukuchi; Tomoyuki Ikemoto, both of Ohmiya; Yoshiaki Watanabe, Kodaira; Kaoru Sota, Tokorozawa, all of Japan

[73] Assignee: Jouveinal, Paris, France

[21] Appl. No.: 877,355

[22] Filed: Jun. 23, 1986

[30] Foreign Application Priority Data

Jun. 26, 1985 [JP] Japan .................. 60-139276

[51] Int. Cl.[4] .................. A61K 31/57; C07J 7/00; C07J 31/00; C61K 31/56
[52] U.S. Cl. .................. 514/181; 514/179; 260/397.1; 260/397.45
[58] Field of Search .................. 260/397.1, 377.45; 514/179, 181

[56] References Cited

U.S. PATENT DOCUMENTS

| 3,028,400 | 4/1962 | Ruschig et al. | 260/397.1 |
| 3,105,083 | 9/1963 | Lincoln et al. | 260/397.1 X |
| 3,171,844 | 3/1965 | Cross | 260/397.1 |
| 4,335,121 | 6/1982 | Phillipps et al. | 260/397.1 X |
| 4,427,671 | 1/1984 | Torossian et al. | 260/397.45 |
| 4,488,995 | 12/1984 | Varma | 260/397.45 |

FOREIGN PATENT DOCUMENTS

| 0141684 | 5/1985 | European Pat. Off. | 260/397.45 |
| 1475795 | 6/1977 | United Kingdom | 260/397.45 |

OTHER PUBLICATIONS

Bordwell et al., J. Amer. Chem. Soc., vol. 73, p. 5004 (1951).
Shirley et al., J. Amer. Chem. Soc., vol. 73, pp. 4885 to 4886 (1951).
Theilheimer, "Synthetic Methods of Organic Chemistry", vol. 16, p. 52, #107 (1962).

Primary Examiner—Floyd D. Nigel
Attorney, Agent, or Firm—Cushman, Darby & Cushman

[57] ABSTRACT

A 21-substituted thiosteroid represented by the general formula

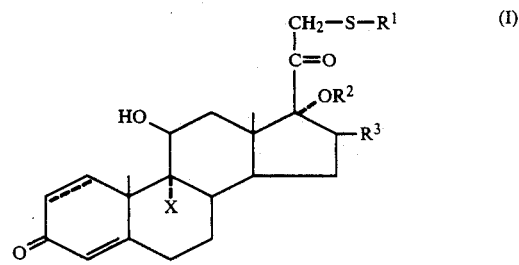

wherein
$R^1$ represents an alkyl group having 1 to 6 carbon atoms, a cycloalkyl group having 5 or 6 carbon atoms, a phenyl group, or a benzyl group which may have a substituent on the benzene ring,
$R^2$ represents an alkanoyl group having 2 to 6 carbon atoms,
$R^3$ represents a hydrogen atom or a methyl group,
X represents a hydrogen or halogen atom, and
the dotted line between 1- and 2-positions represents an optional bond. These compounds are useful an anti-inflammatory agents.

9 Claims, No Drawings

21-ALKYL-, CYCLOALKYL- OR ARYL-SUBSTITUTED THIS STEROIDS AND PHARMACEUTICAL COMPOSITIONS CONTAINING THEM

This invention relates to novel steroidal compounds, and more specifically, to 21-substituted thiosteroids having much reduced systemic side-effects in spite of their excellent anti-inflammatory activity.

Derivatives of corticosteroids resulting from substitution of sulfur for oxygen in the 21-hydroxymethyl group thereof have been reported in some publications. For example, British Patent No. 1,475,795, U.S. Pat. No. 4,427,671 and European Patent No. 141,684 disclose esters of 21-thiolcorticosteroid.

Various corticosteroids have previously been used for the prevention, therapy and treatment of dermatitis, asthma, allergic diseases, rheumatoid, arthritis, etc. as adrenocorticohormones. These adrenocorticosteroids, however, produce systemic side-effects in, for example, topical administration, and give rise to a serious clinical problem.

In the dermatological field, for example, strong external steroidal agents have been developed and frequently used. These agents have been administered in large doses over an extended period of time, and moreover, the occlusion therapy intended to increase the amount of their absorption through the skin has been developed. As a result, various hitherto-inconceivable cases of systemic side effects after absorption through the skin have been reported. They include, for example, Cushing's symptoms, growth inhibition in infants, increase of the blood sugar level and disorders of lipid metabolism.

Such systemic side-effects are generally more prone to develop and become severer with steroids having stronger clinical therapeutic effects. Hence, the careless and excessive use of strong steroidal agents should be avoided, and the type of a steroidal agent to be administered should be carefully selected by considering the type and severity of the disease, the age of the patient, complications, etc.

It has therefore been strongly desired to develop steroidal agents having strong topical therapeutic effects and yet reduced systemic side-effects after absorption through the skin.

It is a primary object of this invention to provide novel 21-substituted thiocorticosteroids having very weak systemic side-effects in spite of exhibiting strong anti-inflammatory activity in topical administration.

Another object of this invention is to provide a process for producing the 21-substituted thiocorticosteroids.

Still another object of this invention is to provide a pharmaceutical composition having anti-inflammatory activity comprising such a 21-substituted thiocorticosteroid as an active ingredient.

Other objects of this invention along with its advantages will become more apparent from the following description.

According to this invention, there is provided a 21-substituted thiosteroid represented by the general formula (I)

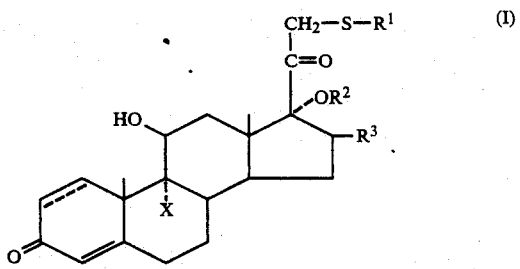

wherein
$R^1$ represents an alkyl group having 1 to 6 carbon atoms, a cycloalkyl group having 5 or 6 carbon atoms, a phenyl group, or a benzyl group which may have a substituent on the benzene ring,
$R^2$ represents an alkanoyl group having 2 to 6 carbon atoms,
$R^3$ represents a hydrogen atom or a methyl group,
X represents a hydrogen or halogen atom, and
the dotted line between 1- and 2-positions represents an optional bond.

In the present invention, the term "alkyl group" denotes a linear or branched saturated aliphatic hydrocarbon group.

The "alkyl group having 1 to 6 carbon atoms" represented by $R^1$ in formula (I) includes, for example, methyl, ethyl, n-propyl, isopropyl, n-butyl, sec-butyl, iso-butyl, tert-butyl, n-pentyl and n-hexyl groups. The alkyl groups having 1 to 4 carbon atoms are preferred. Examples of the "cycloalkyl group having 5 or 6 carbon atoms" are cyclopentyl and cyclohexyl groups.

Examples of the substituent in the "benzyl group which may optionally have a substituent on the benzene ring" include halogen atoms and alkyl groups having 1 to 4 carbon atoms such as methyl and ethyl groups. The benzene ring may be substituted by one or more, preferably one, of such substituents. Examples of the substituted or unsubstituted benzyl groups are therefore benzyl, p-chlorobenzyl and methylbenzyl groups.

The "alkanoyl group having 2 to 6 carbon atoms" represented by $R^2$ in formula (I) denotes a

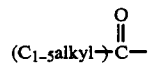

group in which the alkyl moiety has the above meaning. Specific examples of the alkanoyl group having 2 to 6 carbon atoms are acetyl, propionyl, butyryl, isobutyryl, valeryl and isovaleryl groups. The $C_{2-5}$ alkanoyl groups are especially preferred.

The "halogen atom", as used in the present specification, includes fluorine, chlorine, bromine and iodine atoms. The fluorine and chlorine atoms are preferred.

A preferred group of the compounds of formula (I) provided by this invention include compounds of the following formula (Ia)

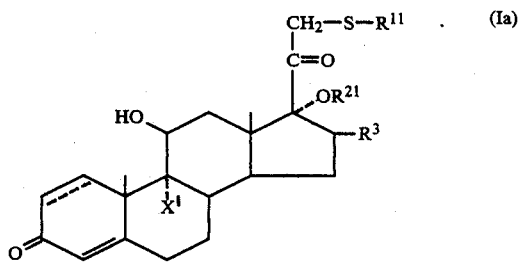

wherein

R[11] represents an alkyl group having 1 to 4 carbon atoms, a cyclopentyl group, a cyclohexyl group, a phenyl group, or a benzyl group which may have a halogen atom or a $C_{1-4}$ alkyl group on the benzene ring, R[21] represents an alkanoyl group having 2 to 5 carbon atoms, X' represents a hydrogen, fluorine or chlorine atom, and R[3] and the dotted line are as defined above.

More preferred among the compounds of formula (Ia) are compounds of the formula (Ia) in which R[11] represents an alkyl group having 1 to 4 carbon atoms, a phenyl group, a benzyl group, a p-chlorobenzyl group, or a p-methylbenzyl group. Especially preferred among the compounds of formula (Ia) from the viewpoint of anti-inflammatory activity and systemic side-effects are those in which R[11] is a methyl, ethyl, isopropyl, phenyl or p-methylbenzyl group, and R[21] is an propionyl or butyryl group.

According to this invention, the 21-substituted thiosteroid of formula (I) can be produced by reacting a 21-sulfonyloxysteroid represented by general formula (II)

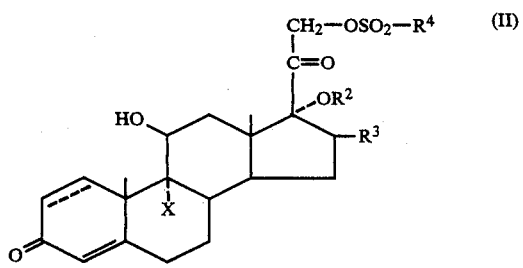

wherein R[4] represents an alkyl group having 1 to 6 carbon atoms, a substituted or unsubstituted aryl group, or a substituted or unsubstituted aralkyl group, and R[2], R[3] and X are as defined above,
with a mercaptan derivative represented by the formula (III)

R[1]—SM         (III)

wherein M represents an alkali metal atom, and R[1] is as defined above.

The 21-alkylsulfonyloxy steroid of formula (II) used as a starting material in the above reaction is a known compound, and can be synthesized, for example, by the process described in U.S. Pat. No. 3,721,687. The unsubstituted or substituted aryl group represented by R[4] in formula (II) is, for example, phenyl, tolyl, or p-bromobenzyl. The unsubstituted or substituted aralkyl group includes benzyl.

The reaction between the compound of formula (II) and the compound of formula (III) is carried out usually in an organic solvent, for example a ketone such as acetone or methyl ethyl ketone, or an amide solvent such as N,N-dimethylformamide or hexamethylphosphoric triamide, at a temperature of about 0° C. to about 100° C., preferably 0° C. to 30° C. Generally, the reaction can be terminated in 1 to 16 hours.

The amount of the compound of formula (III) used relative to the compound of formula (II) is not strictly limited, and can be varied widely according to the type of the starting material, the reaction conditions, etc. Generally, the compound of formula (III) is conveniently used in an amount of 1.05 to 3 moles, especially 1.2 to 2 moles, per mole of the compound of formula (II).

In the mercaptan derivative of formula (III), examples of the alkali metal represented by M are lithium, potassium and sodium. Sodium is especially preferred.

The compound of formula (I) formed by the above reaction can be separated from the reaction mixture and purified by column chromatography and recrystallization.

The 21-substituted thiosteroids of formula (I) provided by this invention have marked pharmacological properties characterized by excellent anti-inflammatory activity and much reduced systemic side-effects. These desirable pharmacological properties are demonstrated by the following animal experiment.

The inhibition of granuloma formation and thymolytic action were examined as a local anti-inflammatory action and a systemic side-effect respectively by the felt pellet granuloma method.

The test was carried out using Wistar strain male rats (body weight 170–200 g), 8 to 10 rats per group, in accordance with the Winter et al. method [J. Pharmacol. Exp. Ther., 141, 369 (1963)].

An ethanol solution (0.05 ml) of the test compound was injected into 20±1 mg of felt pellets to be inserted as the foreign material. Methanol was removed by drying, and then one felt pellet was inserted into each of two subcutaneous sites of the abdomen of each rat. To the rats of a control group, felt pellets treated with only methanol as above were inserted. The dose was 0.001 mg of the test compound per pellet for local anti-inflammatory action, and 0.5 mg of the test compound per pellets for thymolytic action. Seven days after the insertion of the felt pellets, the rats were killed. The granuloma was taken out together with the felt pellet, and dried at 70° C. for 24 hours. The total weight was then measured. The weight of the granuloma was obtained by subtracting the weight of the felt pellet from the total weight. Separately, the weight of the thymus was measured, and the weight of the thymus per 100 g of body weight was calculated. The weight of the granuloma, and the weight of the thymus per 100 g of body weight were compared with those of the control group, and the granuloma inhibition rate (anti-inflammatory action) and the thymolysis rate (systemic side-effect) were calculated.

As comparative drugs, betamethasone 17-valerate (A), hydrocortisone 17-butyrate 21-thioacetate (B), and hydrocortisone 17-butyrate 21-thiopropionate (C) were used.

The results are shown in Table 1.

The results given in Table 1 demonstrate that the compounds of formula (I) provided by this invention have a high granuloma inhibition rate and a low thymolysis rate.

TABLE 1

| Compound No. | Granuloma inhibition rate (%) (0.001 mg/pellet) | Thymolysis rate (%) (0.5 mg/pellet) |
|---|---|---|
| 2 | 46 | −2 |
| 3 | 60 | 9 |
| 5 | 63 | 9 |
| 6 | 61 | 6 |
| 9 | 69 | 9 |
| 14 | 50 | 11 |
| 16 | 73 | 14 |
| 17 | 73 | 11 |
| 19 | 75 | 24 |
| 20 | 79 | −4 |
| 21 | 64 | 5 |
| A | 60 | 65 |
| B | 4 | 13 |
| C | 8 | 7 |

As is clearly seen from the results of the animal experiment described above, the 21-substituted thiosteroids of formula (I) provided by this invention have anti-inflammatory activity equivalent to, or stronger than, betamethasone 17-valerate known as a standard anti-inflammatory agent, and yet have much less systemic side-effects than betamethasone 17-valerate.

Accordingly, the compounds of formula (I) in accordance with this invention can be used as an anti-inflammatory agent for the prevention, therapy and treatment of inflammatory diseases such as dermatitis, asthma, allergic diseases, rheumatoid and arthritis. For these purposes, the compounds of formula (I) are administered topically in conventional dosage forms such as ointments, creams, lotions, liquid coatings and plasters prepared according to conventional pharmaceutical practice. Carriers may be used which are normally used in the production of drugs for topical administration. Examples include fats of the animal origin, vegetable oils, saturated or unsaturated fatty acids, polyhydric alcohols such as glycerol, propylene glycol and polyethylene glycol, waxes, aliphatic hydrocarbons, and water.

The amount of the compound (I) in the above conventional dosage form may be in the range of 0.01 to 5.0% by weight, preferably 0.05 to 2.0% by weight.

The following Examples illustrate the present invention more specifically.

EXAMPLE 1

Hydrocortisone 17-butyrate 21-methanesulfonate (1.67 g) was dissolved in 20 ml of anhydrous acetone, and 1.52 ml of an about 15% aqueous solution of methylmercaptan sodium salt were added. The mixture was stirred at 0° to 5° C. for 1.5 hours. Then, acetone was evaporated, and ice water was added to the residue. The mixture was extracted with ethyl acetate. The organic layer was washed with a 10% aqueous solution of sodium carbonate and water, dried over anhydrous magnesium sulfate, and evaporated to dryness under reduced pressure. The resulting crude product was chromatographed on a silica gel column using chloroform as an eluent to give 1.40 g of hydrocortisone 17-butyrate 21-methylthioether (compound No. 1).

m.p. 138°–142° C. (recrystallized from hydrous ethanol)

EXAMPLE 2

Ethylmercaptan (426 mg) was dissolved in 10 ml of anhydrous acetone, and 370 mg of sodium methylate were added. The mixture was stirred at room temperature for 30 minutes. Then, a solution of 1.75 g of hydrocortisone 17-butyrate 21-methanesulfonate in 10 ml of anhydrous acetone was added, and the mixture was stirred at room temperature for 4 hours. The reaction mixture was let stand overnight, and acetone was evaporated. Water was added to the residue, and the mixture was extracted with ethyl acetate. The extract was worked up in the same way as in Example 1 to give 0.85 g of hydrocortisone 17-butyrate 21-ethylthioether (compound No. 2) as a colorless crystalline powder m.p. 63°–67° C. (recrystallized from hydrous ethanol)

EXAMPLE 3-23

By the same procedure as in Example 1 or 2, the compounds shown in Table 2 were obtained.

TABLE 2

| Compound No. | Compound name | m.p. (°C.) |
|---|---|---|
| 3 | hydrocortisone 17-butyrate 21-propylthioether | 63–66 |
| 4 | hydrocortisone 17-butyrate 21-isopropylthioether | 138–140 |
| 5 | hydrocortisone 17-butyrate 21-butylthioether | 70–75 |
| 6 | hydrocortisone 17-butyrate 21-phenylthioether | 68.5–73 |
| 7 | hydrocortisone 17-butyrate 21-benzylthioether | 139–141 |
| 8 | hydrocortisone 17-butyrate 21-(p-chlorobenzyl)thioether | 185–188 |
| 9 | hydrocortisone 17-butyrate 21-(p-methylbenzyl)thioether | 173–175 |
| 10 | hydrocortisone 17-butyrate 21-cyclopentylthioether | 177–180 |
| 11 | hydrocortisone 17-butyrate 21-cyclohexylthioether | 191–196 |
| 12 | betamethasone 17-propionate 21-methylthioether | 164–167 |
| 13 | betamethasone 17-propionate 21-propylthioether | 190–197 |
| 14 | betamethasone 17-propionate 21-butylthioether | 148–150 |
| 15 | betamethasone 17-butyrate 21-methylthioether | 149–152 |
| 16 | betamethasone 17-valerate 21-methylthioether | 91–93 |
| 17 | betamethasone 17-valerate 21-henylthioether | 80–83 |
| 18 | betamethasone 17-isovalerate 21-methylthioether | 102–105 |
| 19 | beclomethasone 17-butyrate 21-methylthioether | 204–207 |
| 20 | beclomethasone 17-butyrate 21-ethylthioether | 191–193 |
| 21 | beclomethasone 17-butyrate 21-isopropylthioether | 199–202 |
| 22 | beclomethasone 17-butyrate 21-butylthioether | 81–84 |
| 23 | beclomethasone 17-propionate 21-methylthioether | 218–221 |

EXAMPLE 24

White Vaseline (94.4 g) and 0.5 g of Nikkol S010 (sorbitan monooleate) were melted at 70° C. to prepare an oil component. Then, 0.1 g of hydrocortisone 17-butyrate 21-phenylthioether was dissolved in 4.0 g of propylene glycol at 60° C., and the solution was added to the oil component. Furthermore, 1.0 g of plurified water was added, and the mixture was stirred to disperse the ingredients fully. The mixture was cooled with stirring to form 100 g of an ointment.

What we claim is:

1. A 21-substituted thiosteroid having the formula

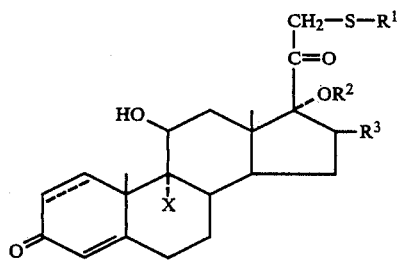

wherein $R^1$ represents alkyl having 1-6 carbon atoms, cycloalkyl having 5 or 6 carbon atoms, phenyl, benzyl or benzyl substituted on the benzene ring, $R^2$ represents alkanoyl having 2-6 carbon atoms, $R^3$ represents hydrogen or methyl, X represents hydrogen or halogen and the bond between positions 1 and 2 is a single bond or a double bond as represented by the dotted line.

2. A compound according to claim 1 having the formula

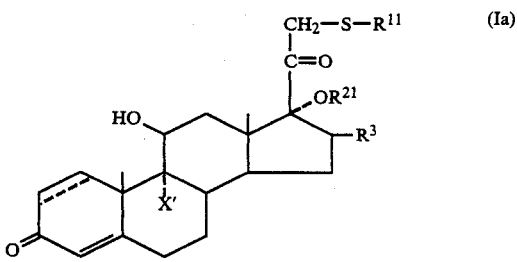

wherein $R^{11}$ represents alkyl having 1-4 carbon atoms, cyclopentyl, cyclohexyl, phenyl, benzyl or benzyl substituted on the benzene ring with halogen or $C_1$-$C_4$ alkyl, $R^{21}$ represents alkanoyl having 2-5 carbon atoms and $X$, represents hydrogen, fluorine or chlorine.

3. The compound of claim 2 wherein $R^{11}$ represents alkyl having 1-4 carbon atoms, phenyl, benzyl, p-chlorobenzyl or p-methylbenzyl.

4. The compounds of claim 1 wherein $R^1$ represents methyl, ethyl, isopropyl, phenyl or p-methylbenzyl and $R^2$ represents ethyl, propyl or butyl.

5. A pharmaceutical composition comprising a compound of formula (I) given in claim 1 and a pharmaceutically acceptable carrier or diluent.

6. An anti-inflammatory agent comprising a compound of formula (I) given in claim 1.

7. Use of a compound of formula (I) given in claim 1 for controlling or preventing illness.

8. Use of a compound of formula (I) given in claim 1 for controlling inflammation.

9. Use of a compound of formula (I) given in claim 1 for the production of a pharmaceutical composition having anti-inflammatory activity.

* * * * *